US005922011A

United States Patent [19]

Cuccia

[11] Patent Number: 5,922,011

[45] Date of Patent: Jul. 13, 1999

[54] MULTI-FUNCTION CHIROPRACTIC TREATMENT TABLE

[76] Inventor: David F. Cuccia, 227 Jackson Ave, Syosset, N.Y. 11791

[21] Appl. No.: 08/874,168

[22] Filed: Jun. 13, 1997

[51] Int. Cl.$^6$ .......................................... A61F 5/00

[52] U.S. Cl. .......................................... 606/241; 606/244

[58] Field of Search .......................................... 606/241–247; 602/32–36; 5/662, 658

[56] References Cited

U.S. PATENT DOCUMENTS 4,915,101 4/1990 Cuccia .......................................... 606/244
5,176,706 1/1993 Lee .......................................... 606/241
5,512,040 4/1996 Mathews .......................................... 606/241

*Primary Examiner*—Michael Buiz
*Assistant Examiner*—Kevin Truong
*Attorney, Agent, or Firm*—M. K. Silverman

[57] ABSTRACT

A multi-function chiropractic treatment table for effecting extension, flexion, lateral flexion and distraction of the spine of a patient. The table includes a weighted platform adapted to rest upon a floor, and telescoping vertical elevation units having upper and a lower ends, each upper end secured to a transverse horizontal pivot axis, the lower end integrally secured to the weighted platform. The table further includes a rigid elongate support frame having an upper part and a lower part, the support frame secured to the horizontal pivot axis of the elevation units, the upper part defining a plane tilted convexly relative to a plane defined by the lower part and an assembly means for selectably rotating the rigid support frame upon the transverse horizontal pivot axis. The treatment table also includes an upper torso support assembly mounted upon the upper part of the rigid support frame, the torso assembly including elements for adjustment of a longitudinal angle of the plane relative to a plane defined by the upper part of the support frame and a lower back support assembly mounted upon the lower part of the support frame. Also included is a pair of positionably adjustable arm support units which are located proximally to sides of the upper torso support assembly, the arm support units having a rear portion rotationally secured to the upper part of the rigid support frame.

22 Claims, 8 Drawing Sheets

MULTI-FUNCTION CHIROPRACTIC TREATMENT TABLE

REFERENCE TO DOCUMENT DISCLOSURE

This application corresponds in subject matter to that of Document Disclosure Number 405,552, filed Sep. 23, 1996.

BACKGROUND OF THE INVENTION

The within invention is an improvement of the invention of my U.S. Pat. No. 4,915,101.

Numerous devices, including chiropractic, osteopathic, obstetrical, delivery, x-ray and operating tables, which suspend or position a patient in a unique way for some special purpose, are known in the art.

U.S. Pat. No. 4,292,926 (1981) to Krause presents an apparatus for effecting postural treatment of humans in which the patient, while resting face down on a pivoting platform, can vary the position of his arms, adjust his center of gravity while in suspension and, thereby, affect his posture upon the table.

U.S. Pat. No. 4,568,669 (1971) to Stites discloses a posture board wherein the patient is rotated 180 degrees from an initial upright position on his back to one of complete inversion hanging by the ankles. With the body hanging freely, normal gravitational pull is reversed thus causing a therapeutic effect on bone structure, spinal column, muscles, internal organs and body fluids.

U.S. Pat. No. 3,685,511 (1972) to Alvarez describes an apparatus which stretches the backbone of a patient while simultaneously providing beneficial massage to the patient's body.

U.S. Pat. No. 3,081,085 (1963) to De Girolamo similarly shows a health table intended to promote proper posture, accomplished through combined flexing and stretching of the back and spine of the patient while supported on the posture board.

U.S. Pat. No. 4,103,681 (1978) to Shanley similarly discloses a tilting traction apparatus where the patient, again lying on his back, is rotated about a pivot point to treat back injury or postural misalignment.

It is to be appreciated that the success of any device designated to treat lower back dysfunction is in large part dependent on proper positioning of the patient prior to, during, and after treatment. For example, in standard traction therapy, the patient wears a pelvic harness and is positioned supinely (face up) in bed, with the spine slightly flexed and knees bent. Straps or roping which is attached to the harness is then inserted into a pulley mechanism and weights attached at an opposite end causing a desired pulling/traction effect. Such pulling traction force producing an elongation of the spinal column (distraction) and a reduction in internal intervertebral disc pressure. This creates a vacuum phenomenon inside the disc which retracts protruded gelatinous material back into its fibrous casing and off of the spinal nerve roots. With the pain gone and the anatomy restored to its natural state, the traction phase of therapy is complete.

An alternate theory for accomplishing the same result is based on extension, rather than flexion of the spine, to achieve reduced intradiscal pressure, while simultaneously anatomically moving nerve roots away from the herniated disc.

While the general principles of flexion, and axial traction of the spine are known in the art and have been effected in various strap and/or harness arrangements, either alone or in combination with rotating-pivot type tables as are described previously (see U.S. Pat. No. 4,205,665 (1980) to Burton and numerous products illustrated in the 1951 "Tables by Trower" catalog) the inventor has found that both flexion and extension, as well as lateral positioning, can all be beneficial depending upon the patient's particular ailment or condition.

Accordingly, there exists the need for a system which can achieve flexion, extension, lateral flexion and/or distraction (alternatively referred to as traction), and other forms of treatment all conveniently available in one multi-function device. The present invention, being both beneficial to the patient and convenient for the doctor, fulfills this need in a variety of ways. In that the subject treatment table not only enables rotation of a patient about a pivot point, but additionally, permits the relative position of the patient's arms, upper torso, legs, lower back, head and shoulders to be selectably varied through an automatic keypad control. The present invention also allows a complete choice as to prone, supine or lateral positioning of the patient prior to treatment. It further enables the doctor to vary the position of the patient prior to treatment, to vary the position of the patient during treatment, and to vary the degree of tractive force being applied to the patient, by selectably variably rotating the patient platform to increase or decrease the tractional gravitational pull applied to the patient through such rotation of the patient platform. There is further provided a "dynamic lifting" into a variable vertical traction position, i.e., the patient stands upright against the table, supported by an adjustable shoulder, arm and hand support and is lifted off the ground, thereby achieving tractional dynamics related to those described above, namely, lengthening and tensioning of the longitudinal ligaments of the spine with separation and increased spacing of all articulating portions of the spine and weight-bearing joints, again causing the vacuum phenomenon responsible for retracting protruding disc material back within the borders of, a healthy disc while keeping the patient suspended in mid-air, or while the patient remains standing on the weighted patient platform utilizing the weight of the lower extremity, the force of gravity, and selected patient anatomical positioning.

My instant invention therefore defines functionally over the structure of my said U.S. Pat. No. 4,915,101 in the following material respects:

1. Ease of control of the system is accomplished through the use of a multi-button control pads by which each of the functions thereof may be utilized, either singularly or in pre-programmed combinations.

2. Ability to concurrently or sequentially lift and rotate the patient, thus providing various treatment options to the physician, including more effective traction of vertebral segments prior to and during table and patient rotation, thereby reducing stress on articulate vertebral surfaces of patient and obtaining a generally more ergonomic patient interface.

3. Ability to change radius of lower back support assembly, to effectuate varying degrees of lumbar extension, varying degrees of lumbar support, as well as a general mobilization of the lumbar spine (lower back).

4. Enhanced patient safety, through the use of selectable patient strapping and other support means, including a thoracic harness, abdominal strapping, overhead wrist strapping and use of arm support assemblies.

5. Provision of a re-positionable overhead hand gripping bar.

6. Provision of upper torso support defining a plane which is adjustable relative to plane of lower back support.

SUMMARY OF THE INVENTION

A multi-function chiropractic treatment table for effecting extension, flexion, lateral flexion, and distraction of the spine of a patient, the table includes a weighted platform adapted to rest upon a floor, and extensible vertical elevation means having an upper end and a lower end, said upper end including a transverse horizontal pivot axis, said lower end integrally secured to said weighted platform. The table further includes a rigid elongate support frame having an upper part and a lower part, said support frame secured to said horizontal pivot axis of said elevation means, said upper part defining a plane tilted convexly relative to a plane defined by said lower part and means for selectably rotating said rigid support frame upon said transverse horizontal pivot axis. The treatment table also includes an upper torso support assembly mounted upon said upper part of said rigid support frame, said assembly including means for adjustment of a longitudinal angle of the plane thereof relative to a plane defined by said upper part of said support frame and a lower back support assembly mounted upon said lower part of said support frame. There is also provided a pair of positionably adjustable arm support means which are located proximally to sides of said upper torso support assembly, said arm support means having a rear portion rotationally secured and selectably positionable to said upper part of said rigid support frame.

A principal object of the invention is to provide a multi-purpose table to effectuate flexion, lateral flexion and distraction of the spine, as may be required in the treatment of spinal disorders and/or maintenance of proper human posture, in such a manner that the relative positions of the patient's arms, legs, lower back, head and shoulders can be varied.

Another object is to provide a treatment table to effectuate extension of the spine, as may be required in the treatment of spinal disorders and/or maintenance of proper human posture, in such manner that the relative positions of the patient's head, upper torso, legs, lower back and can be varied.

Yet another object of the invention to provide a treatment table having a range of motion from zero to at least ninety degrees and, within that range, which can pivot from zero to at least ninety degrees.

A yet further object is to provide a multi-purpose table to provide cervical traction to the neck of a patient.

A still further object is to provide a table which having a variety of pneumatic and other adjustments to permit that patients of widely disparate age, height and weight to be accommodated, without requirement of extended physician set up time.

A yet further object of the invention is to provide a multi-purpose table that is simple to operate, weighted and designed for safety so as not to tip, and constructed of quality materials.

A yet further object is to provide a system in which the position of the upper torso support assembly may be varied relative to the lower back support assembly.

A still further object is to provide a system in which ease of control of substantially all functions, either singly or in combination, may be accomplished through a multi-button, doctor operated control keypad, or to allow patient self-control of all or several selected functions, through additional attachment of selected keypad buttons on either a handgrip bar, overhead horizontal gripping bar or other locations.

It is another object to provide a system that can concurrently or sequentially lift and/or rotate the patient, this providing various treatment options to the physician, including more effective and safer traction of vertebral segments by inducing less stress on articulate vertebral surfaces of patient, and a generally more ergonomic patient interface.

Another use of the table is that of enabling the patient to exercise and strengthen the spine and related musculature to maintain and enhance the health thereof.

Other objects and advantages of the invention will become apparent from the Detailed Description of the Invention, the Drawings and claims appended herewith.

DETAILED DESCRIPTION OF THE INVENTION

With reference to the views of FIGS. 1 through 4, the present chiropractic treatment table for effecting extension, flexion and distraction of the spine of a patient, may be seen to include a weighted platform 10 adapted to rest upon a floor 12, in a typical treatment room of a chiropractor, physical therapist, or other health professionals involved in physical medicine.

Figure 2:
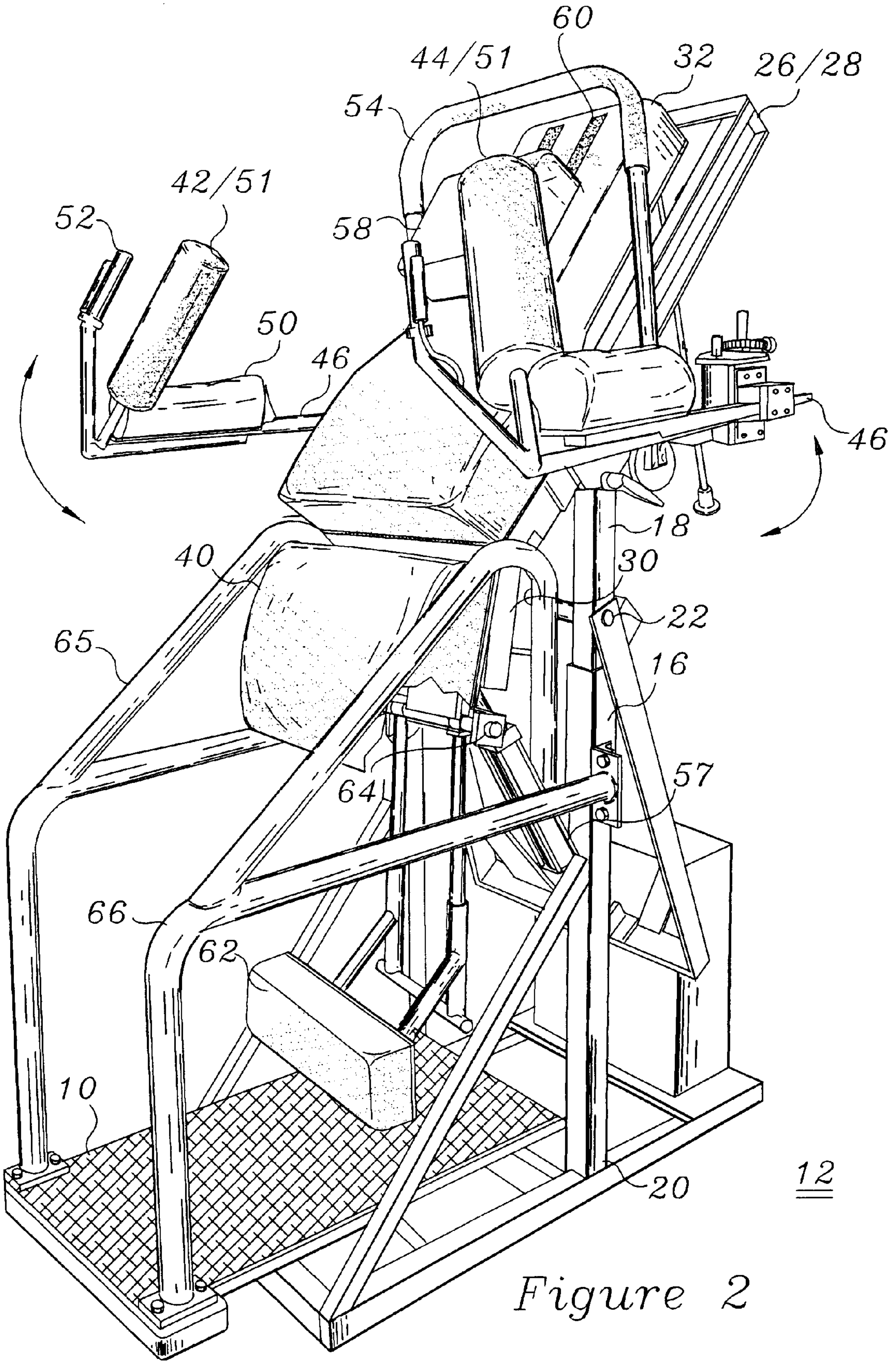
FIG. 2 is a front diagonal view thereof.
Figure 3:
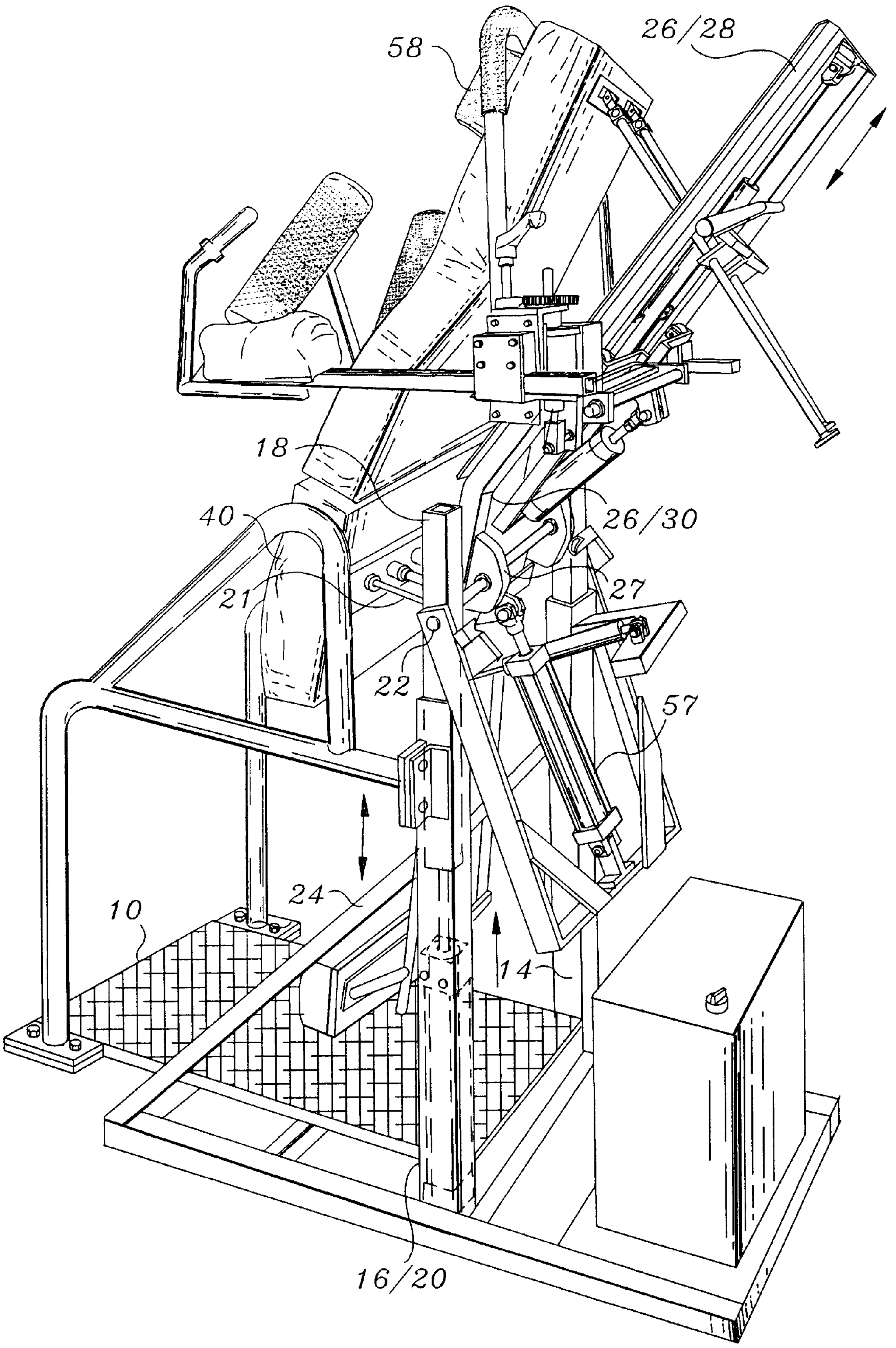
FIG. 3 is a side view of the middle and lower portions of the inventive table.

With reference to FIGS. 2 and 3 the present chiropractic table may be seen to further include a pair of telescoping vertical elevation means 14 and 16, which provide the ability to selectably vertically raise or lower the lower back support assembly that is connected to the rigid support frame 26 to and other dependant attachments to thereby accommodate easily patients of various heights and to effect positioning of such patients on the table.

With reference to FIG. 3, the treatment table may be seen for further include a pair of telescoping vertical elevation means 14 and 16, which preferably comprise extensible hydraulic pistons, each of which means include an upper end 18 and a lower end 20. Said upper end 18 includes, near a free upper end thereof, a transverse horizontal pivot axis 22 which thereby connects the upper ends 18 of each of the vertical elevation means 14 and 16. As may be appreciated from the views of FIGS. 1 through 3, the lower end 20 of each of the vertical elevation means are integrally secured to said weighted platform 10 through the use of diagonal support 24 and other means not shown in the drawings.

The instant multi-purpose treatment table further includes a rigid support frame 26 (see FIGS. 2 and 3) having an upper part 28 and a lower part 30. As may be noted, said lower part 30, of support frame 26 is secured to a block support 27 (see FIGS. 3 and 6) which achieves rotational connection to horizontal pivot axis 22 at the approximate mid point of lowest part 30 thereof. As may be further noted, said upper part 28 defines a plane which is tilted convexly and, preferably, at an angle of about thirty degrees, relative to a plane defined by said lower part 30 of the rigid support frame 26. Such an angle is necessary in that it allows the patient's upper body to be ergonomically supported by the by the upper torso assembly, permitting the back to extend convexly backward at variable selectable angles.

With reference to the view of FIG. 2, the present treatment table may be seen to also include an upper torso support assembly 32 which is mounted upon said upper part 28 of said rigid support frame 26. Said torso support assembly includes means for adjustment of a longitudinal angle 33 (see FIG. 4) of the primary plane thereof relative to a plane defined by said upper part 28 of the support frame 26. This assembly may include a protractor to better measure the angle 33. Said upper torso assembly may be divided or may include moveable sections, with hydraulic or pneumatic piston means or other means for elevation and de-elevation of the upper torso assembly 32. Said assembly may contain an integral air bladder for additional mobilization.

Figure 1:
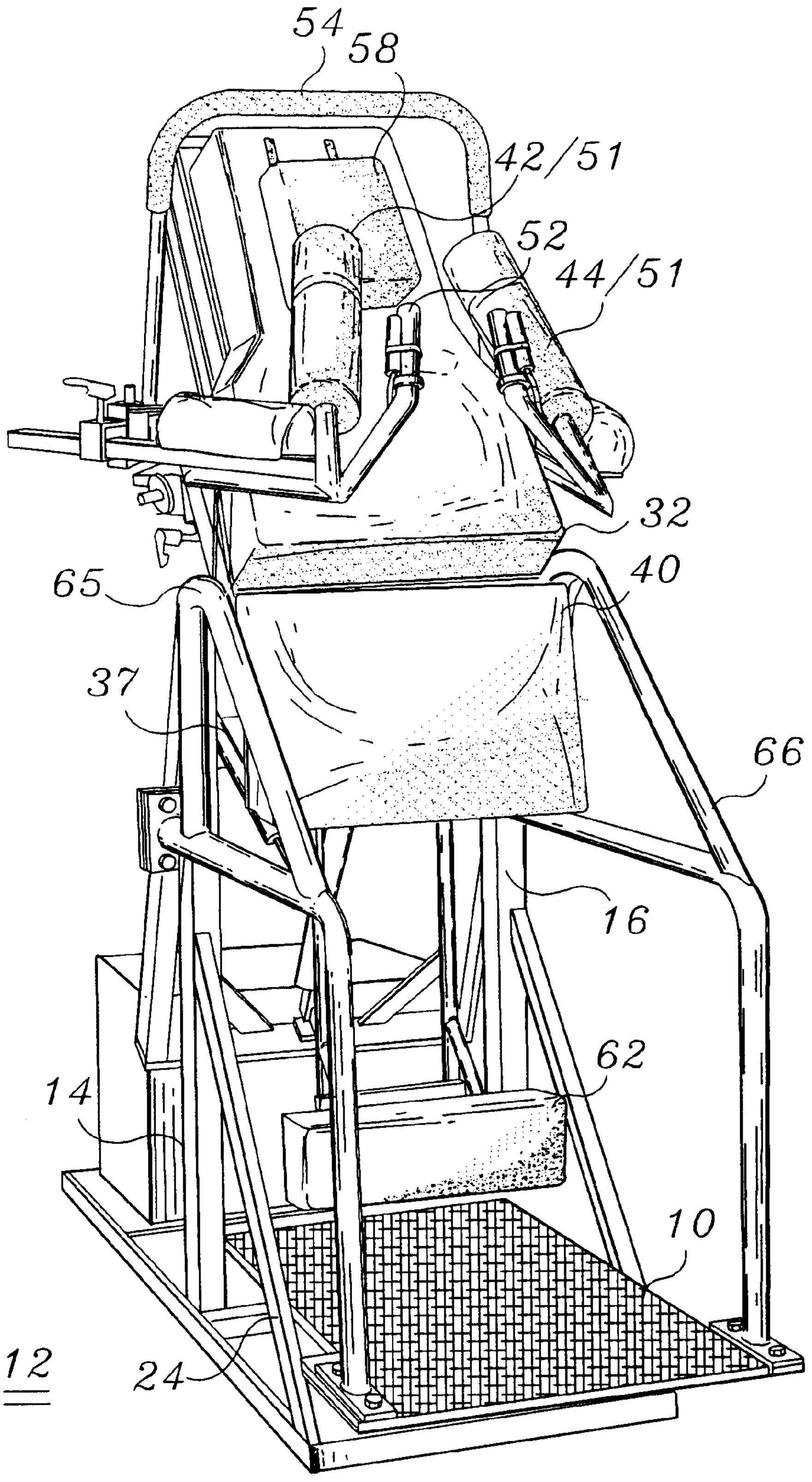
FIG. 1 is a front perspective view of the inventive chiropractic table.
Figure 4:
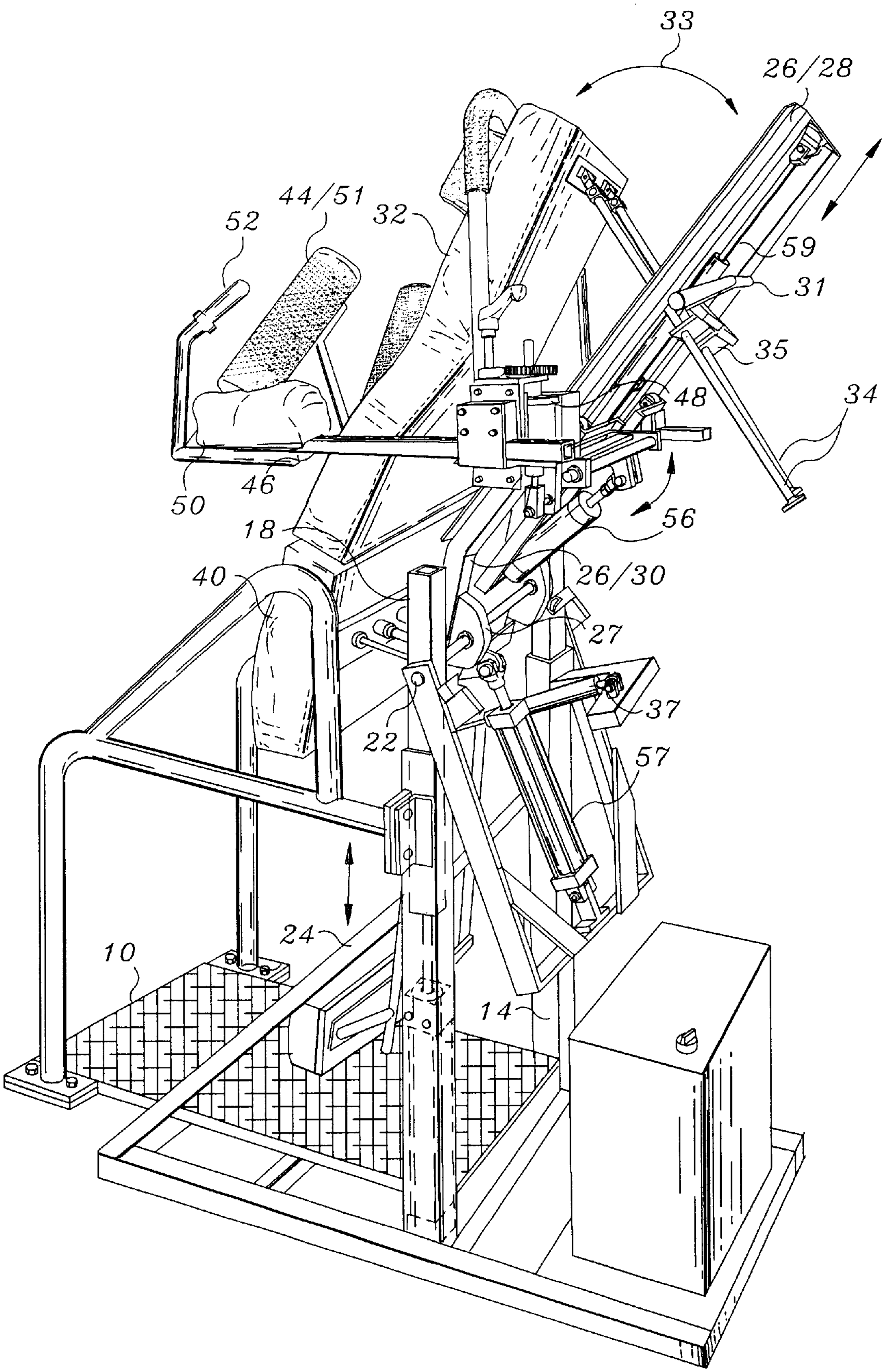
FIG. 4 is a rear diagonal perspective view of the present table.

With reference to the view of FIGS. 1, 2 and 4, the present system may also be seen to include a pair of positionally adjustable arm support means 42 and 44 which are located proximally to the sides of the upper torso support assembly 32. As is set forth below, said arm support means include a selectably adjustable rear portion 46 (see FIGS. 2 and 4) which is rotationally secured by assembly 48 (more fully described below) to said upper part 28 of the rigid support frame 26. See FIG. 6. Said arm support means 42 and 44 include (i) a substantially horizontal arm rests 50; (ii) a chest and shoulder support 51 situated posteriorly and angled inwardly in a patient direction from said arm rest; (iii) a tilted hand grip 52 depending integrally upwardly and inwardly, proximally to said chest and shoulder support 51; and (iv) a transverse overhead horizontal gripping bar 54 at a plane of about ninety degrees relative to that of said horizontal arm rests 50. Each arm support means further includes selectably adjustable means 46 for slidable in and out movement on guide and locking means 55 and selectable securement to, said upper part 28 of the support frame 26. Said means 55 is a part of a rotation enable assembly 48.

Figure 5:
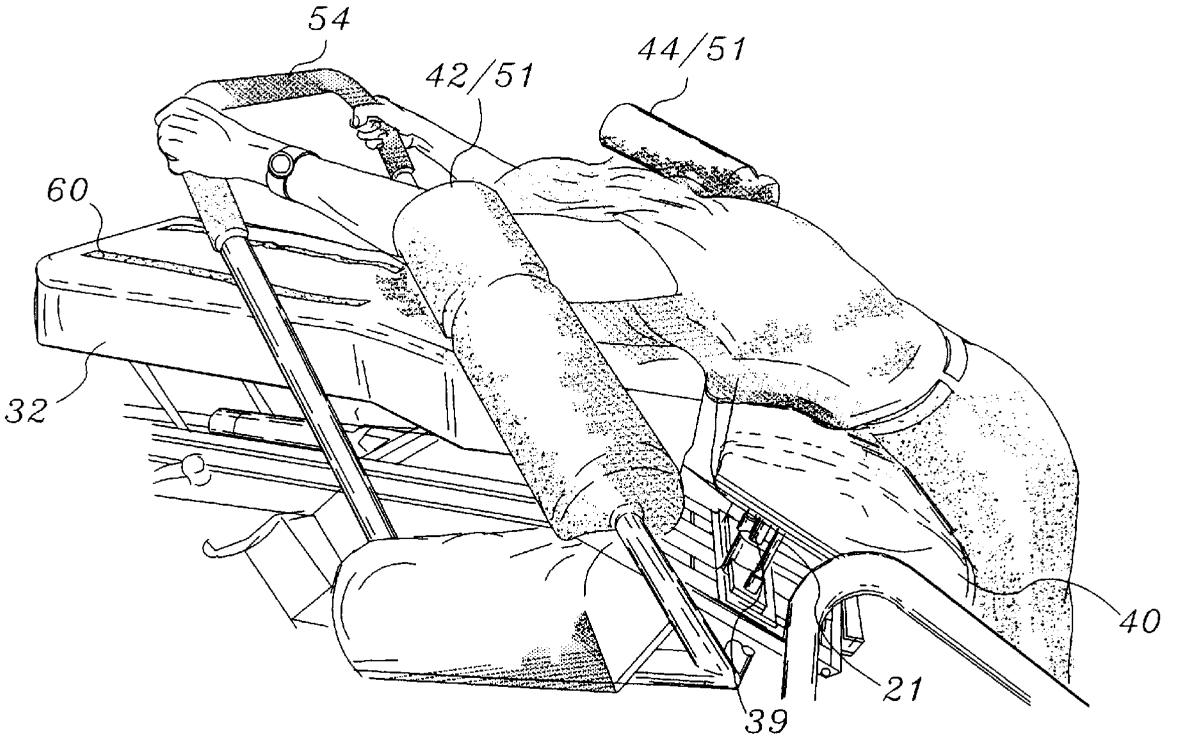
FIG. 5 is an operational view showing one patent positioned on the present table.

With reference to FIGS. 1 through 3, the present treatment table may be seen to further include a lower back support assembly 40 which is connected to telescoping rods 21 (see FIG. 3) and hydraulic rods of hydraulic or pneumatic piston 39 (see FIG. 5) which are secured to lower frame 30 of support frame 26. This provides means for elevation and de-elevation of lower back assembly 40. Said assembly may be provided with means for rotation there of about a vertical axis and may also include an internal air cushion in the form of an inflatable air bladder, for added support and tissue mobilization.

The present table also includes a head rest 58 (see FIGS. 1 and 2) which is positionally adjustable with or without velcro tracks 60 of upper torso support assembly 32.

The system also includes a calf and foot support assembly 62 which integrally depends from an extension 64 of the support frame 26 (see FIGS. 1 and 2). Said assembly is vertically adjustable to accommodate different calf heights.

With reference to FIGS. 3 and 4, the present chiropractic table may be seen to further include an extensible hydraulic or pneumatic piston 57 which comprises means for selectably rotating said rigid support frame 26 upon the transverse horizontal pivot axis 22. This assembly may include a protractor to better measure the degree of rotation. It is, accordingly, to be appreciated that extensible piston 57 thereby facilitates a central function of the present chiropractic table, that is, the rotation of all assemblies attached to the rigid support frame, namely, the upper torso support assembly, the lower back support assembly, and the adjustable arm support means, all through the use of a single control element, namely, extensible pneumatic piston 57.

In FIG. 4 is shown dual rods 34 attached to upper ends 36 thereof to a bottom surface of said upper torso assembly 32 and extending through slide grip means 35 which are controlled by turning of handles 31 (see FIGS. 4 and 6), the same providing said means for adjustments of the angle 33 of the plane of the upper torso support assembly 32 relative to the plane defined by upper part 28 of the elongate support frame 26.

Figure 6:
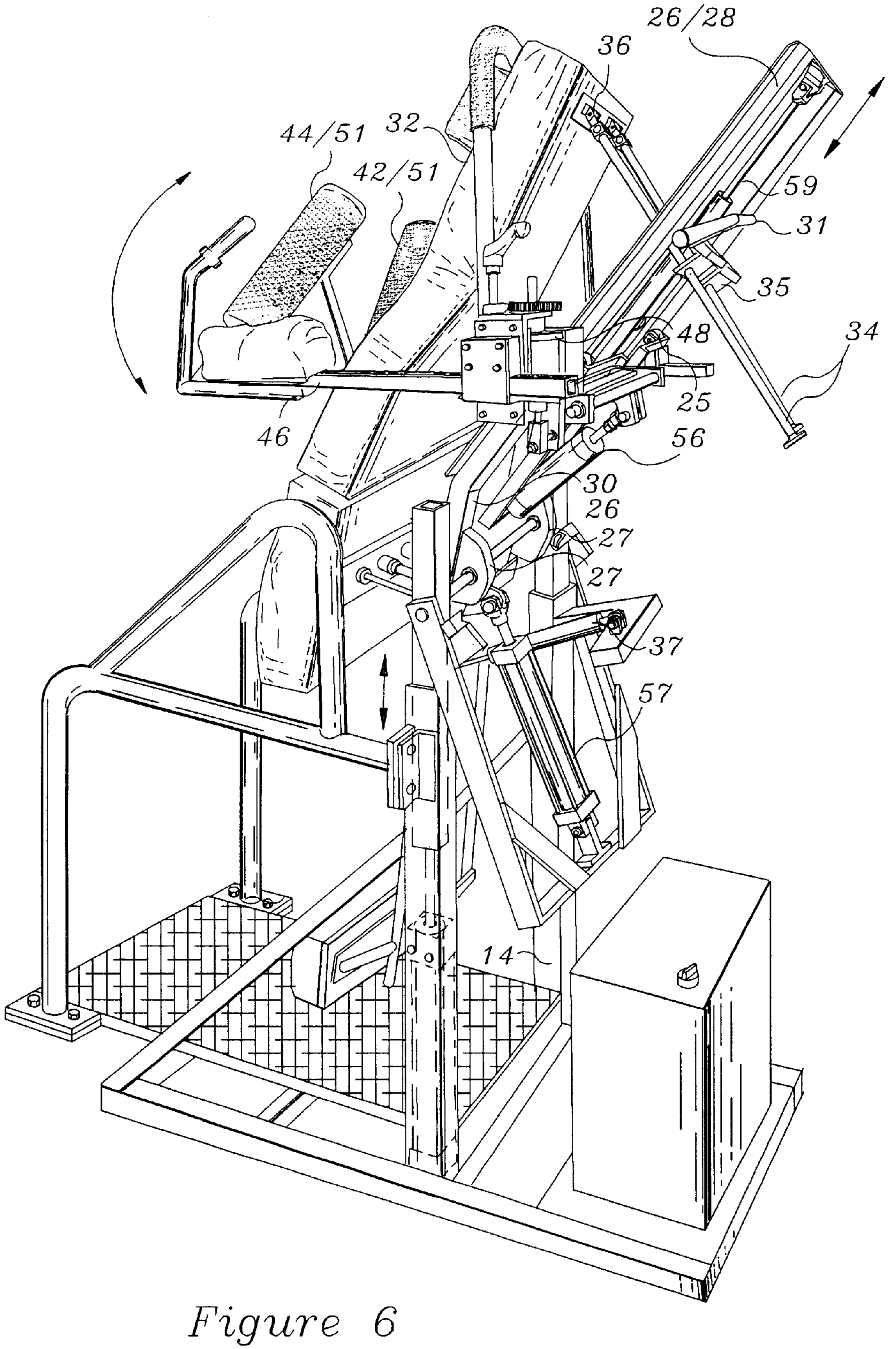
FIG. 6 is a rear perspective view showing various pneumatic cylinder means associated with the present invention.

In FIG. 6 is shown means 59 for effecting selectable translational movement of the arm support means 42 and 44 (see FIG. 6) relative to frame 26, thru an integral roller assembly 25 which is part of arm support means 42 and 44.

It is further noted that said arm support assemblies are selectably rotatable within a vertical plane transverse to a plane defined by the upper part of the support frame 26. Thereby the piston 56 (see FIGS. 4 and 6) of horizontal and vertical parts 50, 51 and 52 of said arm support means 42 and 44 and said transverse gripping bar 54 thereof may be activated causing selectable rotation of arm support assembly within said vertical plane.

Also shown in FIGS. 1 and 2 are safety railing assemblies 65 and 66 which provide a safe railing to enable ease of mounting of a patient onto the weighted platform and which prevents the patient from falling off of the platform prior to and after traction treatment.

Integral or proximal to railings assemblies 65 and 66 may be provided foot push-off bars.

There is provided separate selectable pneumatic or hydraulic piston means 36 (FIG. 8) for the elevation and de-elevation of the lower back support assembly 40. There is also provided a separate piston means 37 (see FIG. 4) for extension or retraction of the calf and foot support assembly.

Figure 7:
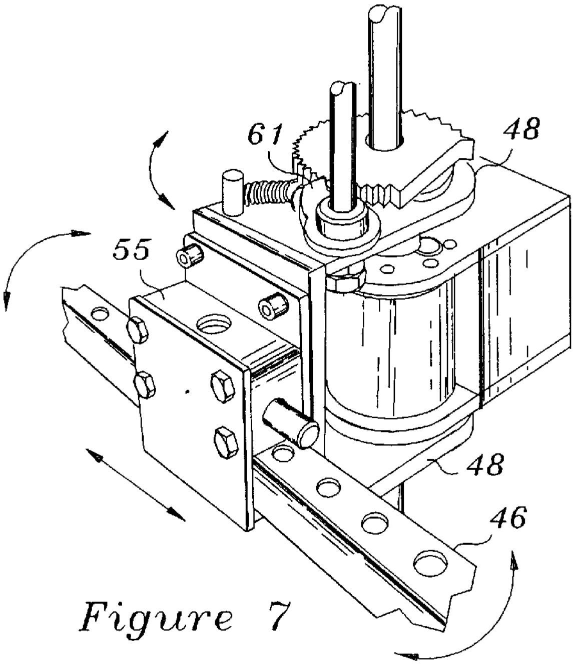
FIG. 7 is an enlarged perspective view of the arm positioning assembly.

Shown in FIG. 7 is the rear of the arm support means 42 and 44, this including rotation enable assembly 48, selectable adjustment means 46, and guide locking means 55.

Figure 8:
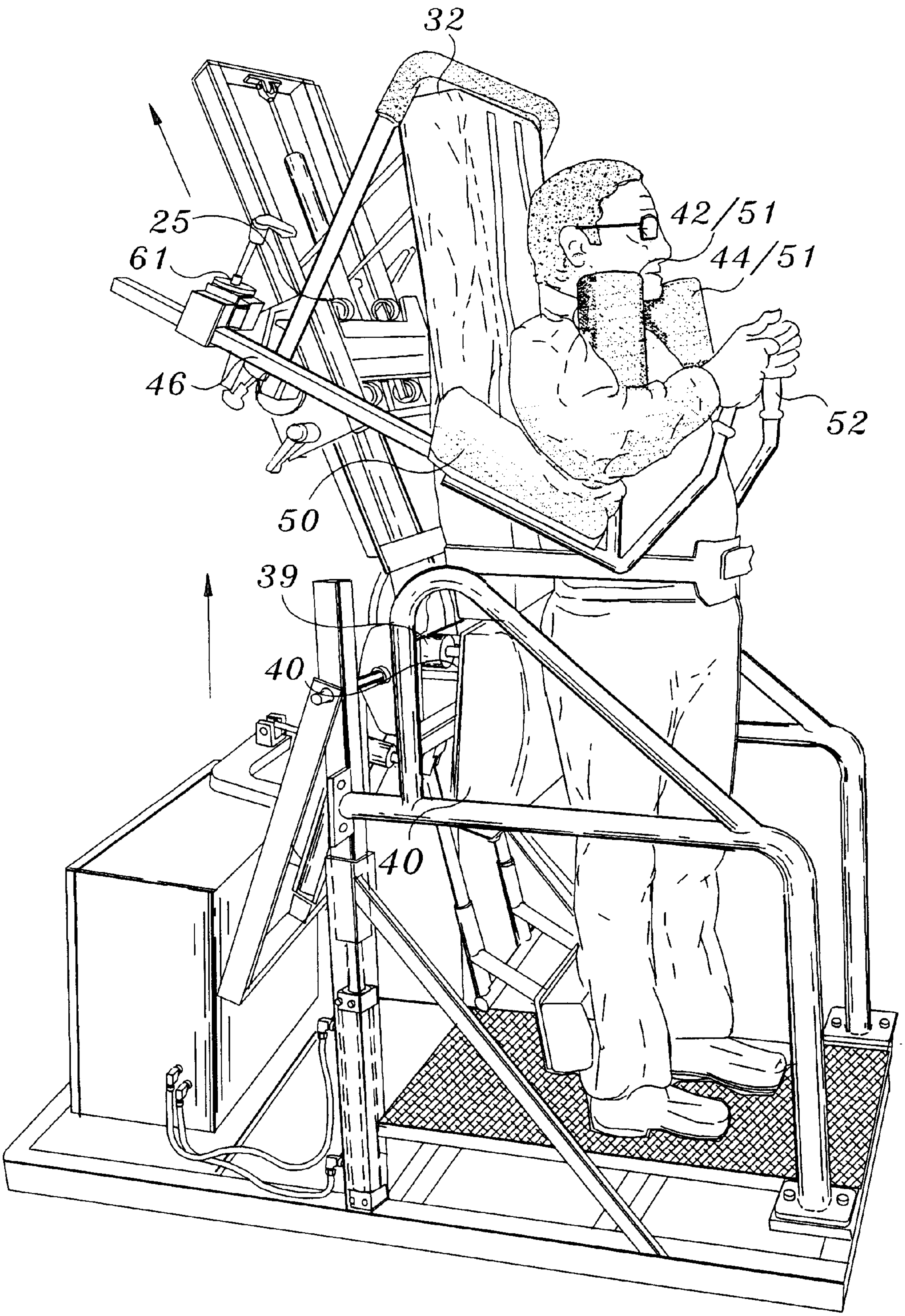
FIG. 8 is a first view of a further embodiment of the invention.

With reference to FIG. 8, there present chiropractic table may be seen to include arm support locking means 61, to prevent outward movement of under arm support means 42 and 44.

Shown in FIG. 8 is a perspective view of a patient making use of shoulder and chest supports 42 and 44 and further showing an embodiment of the invention that includes lower hand grips (52) which, together with the entire assembly, provides safer patient restraint and/or securement while satisfying the patient's inherent need to hold himself in position. The hand grips (52) also allow for convenient mounting of a safety switch and location for auxiliary keypad hydraulic control function switches which would be easily accessible for control by the fingers of the patient. These switches, like those of keypad 74, would enable the doctor and patient control of the table.

With reference to FIG. 8, the upper torso support assembly 32, may also include integral air bladder for tissue mobilization.

Figure 9:
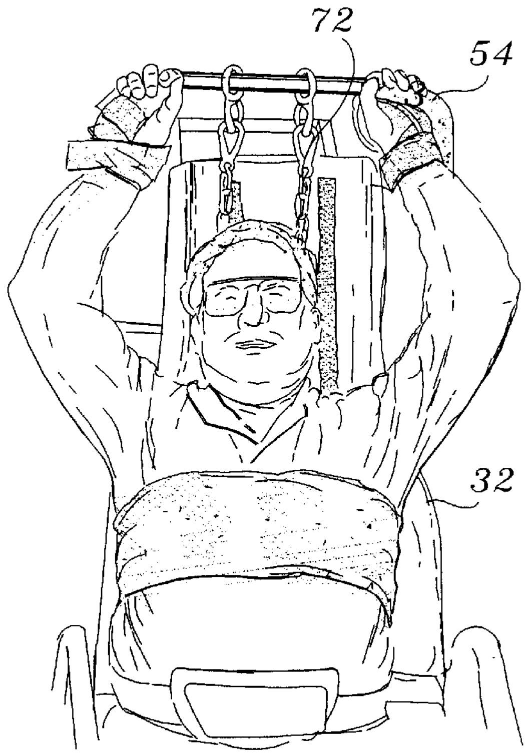
FIG. 9 is a second view of the embodiment of FIG. 8.

In FIG. 9 is shown a further use of the embodiment of FIG. 8, which also shows the use of thoracic traction means 72 which is attached to the overhead arm gripping means (54).

Figure 10:
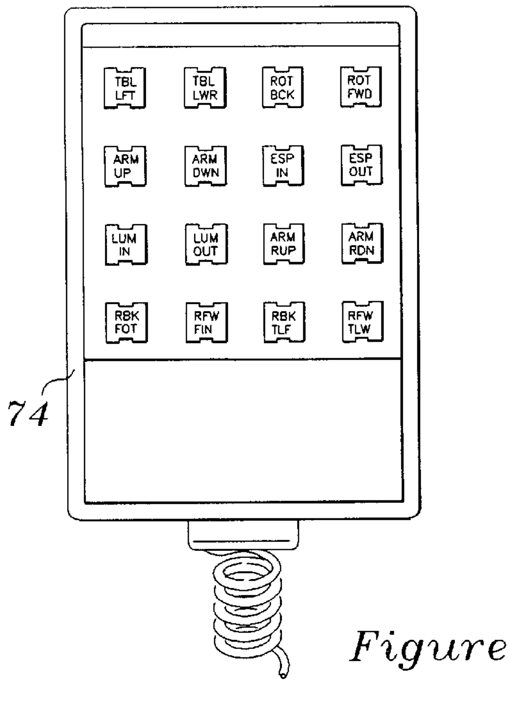
FIG. 10 is a plan view of the system keypad control.

FIG. 10 illustrates a system key pad 74 which includes the following function buttons:

1. TBL LFT=Table Lift.
2. TBL LWR=Table Lower.
3. ROT BACK=Rotate Table Back.
4. ROT FWD=Rotate Table Forward.
5. ARM UP=Translational Arm Height Up.
6. ARM DWN=Translational Arm Height Down.
7. FSP IN=Foot Support In.
8. FSP OUT=Foot Support Out.
9. ARM R. UP=Arm Rotate Up.
10. ARM R. DOWN=Arm Rotate Down.
11. LUM IN=Lumbar In
12. LUM OUT=Lumbar Out
13. R BK FOT=Rotate Table Back with Foot Out. (Calf Support.)
14. R FW FIN=Rotate Table Forward with Foot In (Calf Support.)
15. RBK TL=Rotate Table Back with Table Lift.
16. RFW TLW=Rotate Table Forward with Table and Lower Table.
17. SAFETY ON AND OFF=A safety on and off button is included which stops pneumatic hydraulic motor and ceases all table movement.

The keypad may be programmed for repetitive movements of any function or any function group thereof.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

I claim:

1. A chiropractic treatment table for effecting extension, flexion, distraction and lateral movement of the spine of a patient, the table comprising:

(a) a weighted platform adapted to rest upon a floor;

(b) a rigid elongate support frame having an upper part and a lower part, said upper part defining a plane tilted convexly relative to a plane defined by said lower part;

(c) elevation means including a first end depending integrally upwardly from said platform and having a second end secured to a transverse horizontal pivot axis of said rigid elongate support frame;

(d) an upper torso support assembly mounted upon said upper part of said rigid support frame, said assembly including means for adjustment of a longitudinal angle of a plane thereof generally defined by said upper part of said support frame;

(e) a lower back support assembly mounted upon said lower part of said support frame;

(f) means for selectively rotating said rigid support frame upon said transverse horizontal pivot axis;

(g) a pair of positionably adjustable arm support means located proximal to sides of said upper torso support assembly, said arm support means having a rear portion rotatably secured to said upper part of said rigid support frame; and (h) a chest and shoulder support situated posteriorly of distally located hand grip means, said support positioned substantially vertically and also angled medially and posteriorly in a patient's direction, whereby a chiropractic table is provided to concurrently or sequentially lift and/or rotate the patient, providing various treatment options to the physician.

2. The treatment table as recited in claim 1, in which each of said pair of positionably adjustable arm support means comprises:

(i) a substantially horizontal arm rest; and (ii) a transverse overhead horizontal gripping bar at a plane of about ninety degrees relative to that of said horizonal arm rest.

3. The treatment table as recited in claim 2, in which said pairs of positionably adjustable arm support means may be selectively positioned, lengthened or shortened.

4. The table as recited in claim 1, further comprising:

a titled hand grip depending integrally upwardly and inwardly from a arm rest in a patient direction from said arm rest.

5. The treatment table as recited in claim 1, further comprising:

extensible vertical elevation means having an upper end and a lower end, said upper end including a transverse horizontal pivot axis, said lower end integrally secured to said weighted platform.

6. The treatment table as recited in claim 5, further including cervical neck traction means.

7. The treatment table as recited in claim 1, in which said lower back support assembly further comprises:

pneumatic means for selectable elevation and de-elevation thereof.

8. The treatment table as recited in claim 1, further comprising:

a calf and foot support assembly integrally depending from an extension of said support frame.

9. The treatment table as recited in claim 8, in which said calf and foot support assembly further comprises:

pneumatic means for selectable elevation and de-elevation thereof.

10. The treatment table as recited in claim 1, in which said upper part of said support frame is tilted at an angle of about thirty degrees relative to said lower part thereof.

11. The treatment table as recited in claim 1, wherein said arm support means comprises means for manual adjustment inwardly and outwardly, irrespective of separate vertical positioning or translational movement thereof, having locking and releasing means for additional comfort, safety and of patient securement.

12. The treatment table as recited in claim 1, in which said upper torso support assembly includes:

a hand support assembly longitudinal moveable relative to a fixed base of said torso assembly.

13. The table as recited in claim 1, further comprising:

means for control of table functions including safety and shut-of switches.

14. The treatment table as recited in claim 1 in which said means for selectably rotating said rigid support frame upon said transverse horizontal pivot axis comprises:

pneumatic piston means.

15. The treatment table as recited in claim 1, further including:

means for slidable translation on, and selectably securement to, said arm support means upon said upper part of said elongate support frame.

16. The treatment table as recited in claim 15, in which said adjustable arm support means comprises:

means for selectable rotation thereof within a vertical plane transverse to a plane defined by said elongate support frame, whereby a position of the horizontal and vertical parts of said arm support means and said transverse overhead gripping bar thereof may be selectably rotated within said vertical plane.

17. The treatment table as recited in claim 15, in which said means of rotation of said arm support means comprises:

selectable pneumatic piston means.

18. The treatment table as recited in claim 15, in which a means for selectable translational movement for sliding said arm means upon said support frame further comprises:

selectable pneumatic piston means.

19. A chiropractic treatment table for effecting extension, flexion, distraction and lateral movement of the spine of a patient, the table comprising:

(a) a weighted platform adapted to rest upon a floor;

(b) a rigid elongate support frame having an upper part and a lower part, said upper part defining a plane tilted convexly relative to a plane defined by said lower part;

(c) elevation means including a first end depending integrally upwardly from said platform and having a second end secured to a transverse horizontal pivot axis of said rigid elongate support frame;

(d) an upper torso support assembly mounted upon said upper part of said rigid support frame, said assembly including means for adjustment of a longitudinal angle of a plane thereof generally defined by said upper part of said support frame;

(e) a lower back support assembly mounted upon said lower part of said support frame; and (f) means for selectively rotating said rigid support frame upon said transverse horizontal pivot axis, whereby a chiropractic table is provided to concurrently or sequentially lift and/or rotate the patient, providing various treatment options to the physician.

20. The treatment table as recited in claim 19, in which said chiropractic table further comprises arm support means comprising:

(g) a pair of positionably adjustable arm support means located proximal to sides of said upper torso support assembly, said arm support means having a rear portion rotatably secured to said upper part of said rigid support frame; and (h) means for selectable rotation of said arm support means within a vertical plane transverse to a plane defined by said elongate support frame, whereby horizontal and vertical parts of said arm support means, and said transverse overhead gripping bar thereof, may be selectably rotated within said transverse plane.

21. The treatment table as recited in claim 19, in which said means of rotation of said arm support means comprises:

selectable pneumatic piston means.

22. A chiropractic treatment table for effecting extension, flexion, distraction and lateral movement of the spine of a patient, the table comprising:

(a) a weighted platform adapted to rest upon a floor;

(b) a rigid elongate support frame having an upper part and a lower part, said upper part defining a plane tilted convexly relative to a plane defined by said lower part;

(c) elevation means including a first end depending integrally upwardly from said platform and having a second end secured to a transverse horizontal pivot axis of said rigid elongate support frame;

(d) an upper torso support assembly mounted upon said upper part of said rigid support frame, said assembly including means for adjustment of a longitudinal angle of a plane thereof generally defined by said upper part of said support frame;

(e) a lower back support assembly mounted upon said lower part of said support frame;

(f) means for selectively rotating said rigid support frame upon said transverse horizontal pivot axis; and (g) a calf and foot support assembly integrally depending from an extension of said support frame, said calf and foot support assembly comprising pneumatic means for selectable elevation and de-elevation thereof, whereby a chiropractic table is provided to concurrently or sequentially lift and/or rotate the patient, providing various treatment options to the physician.

* * * * *